United States Patent [19]
Perbellini et al.

[11] Patent Number: 6,140,313
[45] Date of Patent: Oct. 31, 2000

[54] BUTYRIC ESTERS WITH ANTIPROLIFERATIVE ACTIVITY AND THE PHARMACEUTICAL COMPOSITIONS CONTAINING THEM

[76] Inventors: Alberto Perbellini, Via Risorgimento, 23, 37126 Verona, Italy; Danila Coradini, Via A. Pecorini, 7, 20138 Milan, Italy

[21] Appl. No.: 09/308,832

[22] PCT Filed: Nov. 26, 1997

[86] PCT No.: PCT/EP97/06589

§ 371 Date: May 25, 1999

§ 102(e) Date: May 25, 1999

[87] PCT Pub. No.: WO98/23648

PCT Pub. Date: Jun. 4, 1998

[30] Foreign Application Priority Data

Nov. 29, 1996 [IT] Italy .................................. MI96A2505

[51] Int. Cl.[7] ............................ A61K 31/72; C08B 37/00
[52] U.S. Cl. ........................... 514/54; 536/115; 536/118; 536/119; 536/123.12
[58] Field of Search ............................... 536/63, 68, 107, 536/110, 115, 119, 123.12, 122, 118; 514/54

[56] References Cited

U.S. PATENT DOCUMENTS

| | | | |
|---|---|---|---|
| 4,024,334 | 5/1977 | Chandler et al. | 536/65 |
| 4,959,466 | 9/1990 | White | 536/119 |
| 4,981,959 | 1/1991 | Diamantoglou | 536/56 |
| 5,093,486 | 3/1992 | Diamantoglou | 536/20 |
| 5,597,912 | 1/1997 | Edgar et al. | 536/63 |
| 5,717,087 | 2/1998 | Kalbe et al. | 536/32 |
| 5,733,750 | 3/1998 | Lund et al. | 435/72 |
| 5,830,872 | 11/1998 | Baldwin et al. | 514/23 |
| 5,877,144 | 3/1999 | Ehrhardt et al. | 510/470 |
| 5,916,883 | 6/1999 | Shalaby et al. | 514/58 |

OTHER PUBLICATIONS

Eliasson, Ann–Charlotte. Carbohydrates in Food, published by Marcel Dekker, Inc., pp. 366–368, 1996.

Nikitin, N.I. The Chemistry of Cellulose and Wood, pp. 63–66, 1966.

G.F. Feluso et al., The Effect of High and Low Molecular Weight Hyaluronic Acid on Mitogen–Induced Lymphocyte Proliferation, Current Therapeutic Research, vol. 47, No. 3, Mar. 1990.

Studies on Interralation of Structure and Antitumor Effects of Polysaccharides: Antitumor Action of Periodatemodified, Branched (1→3)–β–D–Glucan of *Auricularia auricula–judae*, and other Polysaccharides Containing (1→3)–Glycosidic Linkages., Carbohydrates Research, 92 (1981) 115–129.

Proceedings of the American Association for Cancer Research, vol. 37, Mar. 1996, Monday, Apr. 22, 1996, 1:00–5:00, Poster Section 1.

Julie Dechanet et al., IL–4 Inhibits Growth Factor–Stimulated Rheumatoid Synoviocyte Proliferation by Blocking the Early Phases of the Cell Cycle, The Journal of Immunology, vol. 151, 4908–4917, No. 9, Nov. 1, 1993.

Bernard Levin, Ulcerative Colitis and Colon Cancer: Biology and Surveilance, Journal of Cellular Biochemistry, Supplement of Cellular Biochemistry, Supplement 16G: 47–50 (1992).

C.A. Rubio, MD et al., Crohn's Disease and Adenocarcinoma of the Intestinal Tract, Disease of the Colon & Rectum, vol. 14, No. 2, 174–180.

Gert Storm et al, Liposomes and Biotherapeutiics, Biotherapy 3, 25–42, 1991.

Aya Leder and Philip Leder, Butyric Acid, a Potent Inducer of Erythoid Differation in Cultured Erythroid Differentation in Cultured Erythroleukemic Cells, Cell, vol. 5, 319–322, Jul. 1975.

*Primary Examiner*—Howard C. Lee
*Attorney, Agent, or Firm*—Hedman, Gibson & Costigan

[57] ABSTRACT

The present application describes total or partial butyric esters of polysaccharides as novel compounds; the number of hydroxyl groups esterified with butyric residues per each glycosidic monomer is preferably higher than 0.001; the application also describes the process of preparation of said esters, their use in therapy as antiproliferative agents, and pharmaceutical compositions containing them.

22 Claims, 3 Drawing Sheets

BUTYRIC ESTERS WITH ANTIPROLIFERATIVE ACTIVITY AND THE PHARMACEUTICAL COMPOSITIONS CONTAINING THEM

This application is a 371 of PCT/EP97/06589 filed on Nov. 26, 1997.

FIELD OF THE INVENTION

The present invention relates to new partial or total butyric esters of polysaccharides, with high antiproliferative activity; these esters are therapeutically effective in the treatment and prevention of diseases characterized by abnormal cell proliferation like neoplasms and synovial diseases.

STATE OF THE ART

The biological activity of many classes of polysaccharides was thoroughly studied in relation to their use as drugs for the treatment of different pathologies. Among the polysaccharides used in therapy, heparins with either a low or an high molecular weight, are known as anticlotting agents, while dextrans are notoriously used as plasma expanders.

Recently new biological activities of polysaccharidic compounds have been identified, allowing to foresee a wider use of these polysaccharides in medicine.

Among the polysaccharides that constitute the active compounds of drugs presently in use, it is worth mentioning hyaluronic acid, which is used in the treatment of osteoarthrosis and other pathologies, since it can inhibit the lymphocyte proliferation (G. F. Peluso et al., *Current Therapeutic Research*, 47(3): 437–443, March 1990), and scleroglucan (commercialized as the active compound of a formulation called Sizofiran®) that is used as an immunostimulant in the treatment of some tumors (Eric J. Lien, *Prog. Drug. Disc.*, 34: 395–420, 1990).

Moreover, some drugs of polysaccharidic nature are known in an advanced stage of clinical development, such as, for example, pentosan polysulphate which is used in the treatment of some tumors, and several derivatives of hyaluronic acid which are used as adjuvants in the healing processes and in the prevention of post-surgical adhesions. Results of particular relevance have recently emerged from the search for new pharmacological uses of polysaccharides.

Among the many pharmacological activities exerted by some families of polysaccharides, the antiproliferative activity leads to the possibility to use them as antitumour drugs, since they can inhibit the development of some lines of tumor cells. (A. Misaki et al., *Carbohydrate Research*, 92 (1981): 115–192).

The butyric acid is a compound of natural origin, non toxic, normally present in food and in the gastrointestinal tract as a product of the bacterial fermentation of complex carbohydrates. From a pharmacological viewpoint, this compound exerts an antiproliferative activity, by inhibiting the cell growth and by inducing the differentiation of a large variety of neoplastic cells, as widely shown by experimental tests carried out both in vitro and in vivo on different cell lines. The cell and molecular mechanisms which underlie the differentiating activity of butyric acid have not been fully elucidated so far. In particular, the sodium salt of the butyric acid is a known inducer of cytodifferentiation (A. Leder e P. Leder, *Cell*, 5:319, 1975). However, even though it is endowed with a good antiproliferative potential, the sodium salt of butyric acid exhibits the disadvantage of having a very short half-life, which has, so far, limited its use in vivo and that excludes the possibility of using it as a drug, since it is difficult to obtain sufficient plasma concentrations to exert a therapeutical effect.

As a matter of fact, once it is administered by the intravenous route, the active compound circulates for just 5–6 minutes before being metabolized.

Several attempts to overcome this drawback have been performed;

a chemical attempt aimed at the stabilization of the molecule by means of esterification, so as to delay its degradation and to prolong its biological activity. Some simple esters of butyric acid are in fact known; among these, the phenyl butyrate, which can exert an antineoplastic activity in prostate cancer models (*Proceedings of the American Association for Cancer Research*, vol. 37, March 1996, 498) and in other tumors. In this case, the esterification is simply aimed at increasing the plasma half-life of the active compound by converting the active compound into a prodrug which, by hydrolysis, slowly releases the butyric acid in the target organ. However, the activity of these esters turns out to be always lower than that of the free acid form, since the bioavailability of the active compound is lower. No encouraging results in this direction have emerged.

An interesting alternative to the esterification of butyric acid and to the modification of its chemical structure entails the encapsulation in liposomes that, can provide a better protection to the degradation and a vehicolation of the active compound itself at higher concentrations (G. Storm et al., *Biotherapy*, 3: 25, 1991); even in this case, the results obtained so far are not totally satisfying, because of the low entrapping efficacy exerted by the liposome vesicles.

SUMMARY

The Applicant has prepared new polysaccharide derivatives, both anionic and neutral, which, surprisingly, can inhibit abnormal cell proliferation at an amount notably higher than that of the corresponding unmodified polysaccharide (hereafter called "source polysaccharide"). A new class of butyric esters of polysaccharides is therefore the object of the present invention. These butyric esters can possibly have one or more substituents on the carbon atoms of the glycosidic ring, selected from the group consisting of lower alkyls, $-NH_2$, $-NH-COR$, $-OSO_3H$, $-OPO_3H_2$—COOH, $-COO-$ $(CH_2)_n$ $-COOH$, $-COOR$, $-COR$, $-OR$ e $-O-$ $(CH_2)_n$—O—COR, where n=1–4 and R=alkyl $C_1-C_{10}$, where the hydroxyl groups of these polysaccharides are partially or totally esterified with butyric residues, and the additional free hydroxyl groups of the glycosidic residue are possibly esterified with dicarboxylic residues. Preferably, the number of hydroxyl groups esterified with butyric residues for each glycosidic monomer is higher than 0.001.

A further object of the present invention is a process for the preparation of said butyric esters, including the treatment of said polysaccharides with butyric esters or one of its activated form, possibly in an adequate solvent and/or in the presence of a proper catalyst.

Moreover, the present invention relates to the use of the above butyric esters as antiproliferative agents and new pharmaceutical compositions containing a therapeutically effective amount of at least one of the above butyric esters as an active compound, in combination with excipients and/or solvents pharmaceutically acceptable.

Figure 2:
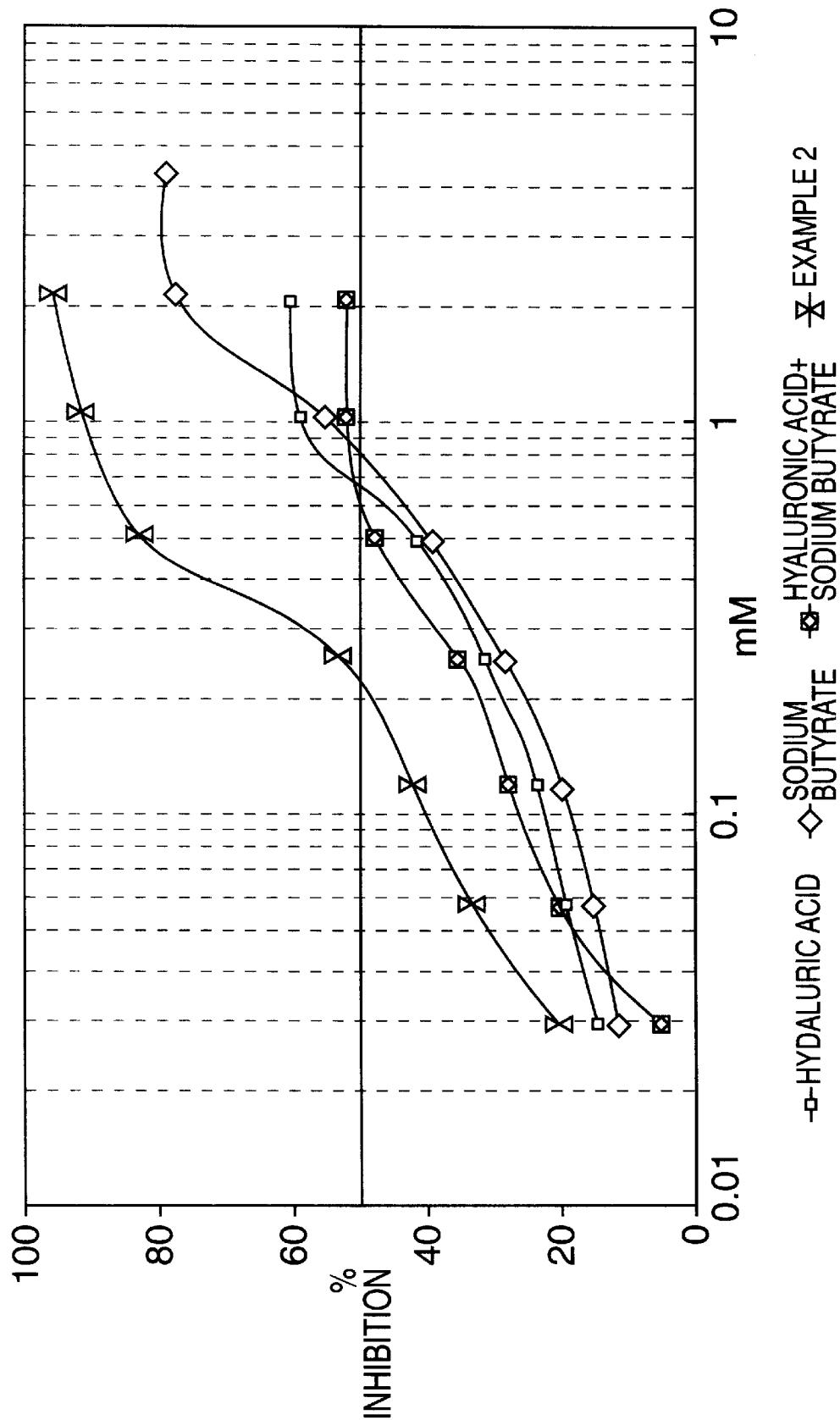

FIG. 2 illustrates the figures reported above in a representation which shows the inhibition percentage of the cell growth vs the concentration of the compounds tested. These figures show that the butyric esters of polysaccharides can exert an antiproliferative activity which is unexpectedly higher than the activity exerted by the mixture of the components.

Figure 3:
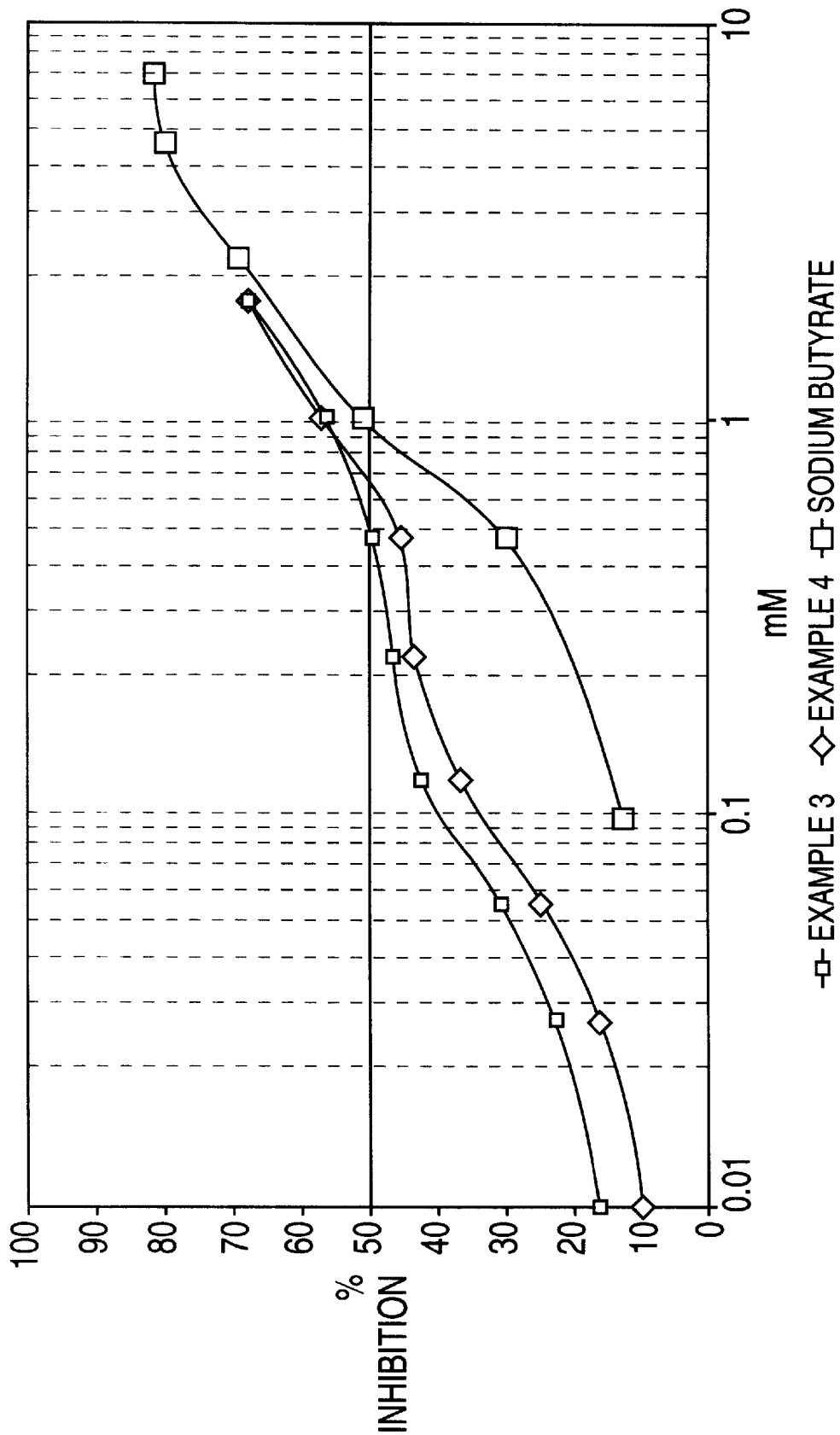

FIG. 3 shows the antiproliferative effect of the butyric ester of Examples 3 and 4 on the growth of the MDA-MB231 cell line, after 6 days of treatment, as a comparison of the effect of sodium butyrate used at the same concentrations and experimental conditions. The diagram shows the inhibition percentage of the cell growth vs the concentration of the compounds tested (the molarity (mM) is referred to the concentration of the butyrate in the compounds examined).

DETAILED DESCRIPTION OF THE INVENTION

The characteristics and the advantages of the new butyric esters of polysaccharides, of the procedure for their preparation, of their therapeutic use and of the pharmaceutical compositions containing them, according to the present invention, will be better elucidated during the following detailed description.

The new butyric esters, according to the present invention, are made up of either totally or partially butyrated polysaccharides, where the number of esterified hydroxyl groups with butyric residues for each glycosidic monomer is preferably higher than 0.001. The butyric residues can range from 1% to 10% by weight with respect to the total weight; the degree of substitution (DS) is preferably in the range from 0.001 to 3 and even more preferably from 0.01 to 1. The term "degree of substitution (DS)" indicates the number of derivatized hydroxyl groups for each glycosidic monomer of the polysaccharide.

The possible additional free hydroxyl groups of the glycosidic residue of said polysaccharides can be esterified with residues of $C_2$–$C_9$ dicarboxylic acids, preferably selected from the group consisting of succinic, tartaric, malic and azelaic acid.

Said butyric esters have an average molecular weight preferably higher than $2 \times 10_3$ and even more preferably in the range from $1 \times 10^4$ to $5 \times 10^6$.

The term "polysaccharides" indicates compounds of a polysaccharidic nature, preferably natural, i.e. isolated from sources of natural origin such as bacteria, fungi, lichens, higher plants, algae, microalgae and shellfish; or, said natural polysaccharides can be obtained from animal (e.g.: roaster comb) and human sources (e.g. from the umbilical cord), as known in the state of the art.

Said polysaccharides can be either linear or branched, where the backbone and its possible side chains contain preferably glycosidic residues selected from the group consisting of D-glucose, D-ribose, D-gulose, D-xylose, D-arabinose, D- and L- mannose, D-galactose, L-fucose, L-rhamnose, D-uronic acid, D-glucuronic acid, D-mannuronic acid, D-guluronic acid, and D-galacturonic acid.

The backbone of said polysaccharide has a $\beta(1\to3)$ or $\beta(1\to4)$-D-glycosidic linkage, or even more preferably glucosidic, or $\alpha(1\to3)$ or $\alpha(1\to4)$ or $\alpha(1\to6)$-glycosidic linkage.

The side chains are preferably made up of single D-glycosidic residues bound in the $\beta(1\to3)$ or $\beta(1\to4)$, $\beta(1\to6)$, or $\alpha(1\to4)$ configuration or even more preferably they are made up of $\beta(1\to6)$ glucosyl residues.

Said polysaccharide can be a $\beta(1\to3)$ -D-glucan, where the term "glucan" indicates a linear polysaccharide with $\beta(1\to3)$-D-glucopyranose residues; said polysaccharides can be $\beta(1\to3)$-D-glucans with $(1\to6)$ sidechains and are preferably selected from the group consisting of scleroglucan which has a $\beta(1\to3)$-D-glucopyranosidic linear backbone with a $\beta(1\to6)$-D-glucopyranosidic side chain per each three glucosidic units of the main chain, lentinan ($\beta(1\to3)$-D-glucosidic bonds), pachimaran ($\beta(1\to3)$-D-glucosidic bonds), curdlan ($\beta(1\to3)$-D-glucosidic bonds) and pullulan ($\alpha(1\to3)$ and $\alpha(1\to6)$-D-glucosidic bonds). The molecular weight of these glucans is preferably in the range from $1 \times 10^4$ to $1 \times 10^6$.

Moreover, on the carbon atoms of the saccharidic residue, said polysaccharides can have one or more substituents selected from the group consisting of lower alkyls, —$NH_2$, —NH—COR, —$OSO_3H$, —$OPO_3H_2$, —COOH, —COO—$(CH_2)_n$—COOH, —COOR, —COR, —OR and —O—$(CH_2)_n$—O—COR, where n=1–4 and R=alkyl $C_1$–$C_{10}$. In this case, the butyric esters of the invention can be possibly salified with cations of alkaline metals (preferably Na and K), alkaline-earth-metals (preferably Ca and Mg) and transition metals (preferably Cu, Zn, Ag and Au). The derivatized polysaccharides can be obtained by chemical modification of natural polysaccharides, according to methodologies known in the state of the art.

Among the carboxylated polysaccharides, hyaluronic acid, made up of alternating residues of D-N-acetyl-glucosamine and D-glucuronic acid, can be profitably used. The molecular weight of hyaluronic acid ranges from $10^4$ to $2 \times 10^6$.

Pectin is a further example of carboxylated polysaccharides useful in the present invention. Pectin is a carboxylated polysaccharide mainly composed of D-galacturonic acid or D-galactose. The carboxyl groups of pectin may be partially present in the form of methyl esters. The molecular weight of pectin varies between $2 \times 10^4$ to $4 \times 10^5$.

A further polysaccharides useful in the invention is alginic acid, composed of $(1\to4)$ -$\alpha$-L-guluronic and $\beta$-D-mannuronic acid, with a molecular weight preferably higher than $10^4$ and preferably in the range from $10^5$ to $10^6$. Other examples are represented by heparins, heparinoids, and carrageenans (algal sulfated polysaccharides).

A natural polysaccharide particularly suitable for obtaining butyric esters according to the present invention is a sulfated polysaccharide isolated from a marine alga, *Grateloupia doryohora* (belonging to the Grateloupiacee family). Also other natural polysaccharides obtained from other algae of the Grateloupiacee species, with D-galactose residues with $(1\to3)$ bonds and with sulfated residues in position 2, 3 and/or 6 can be profitably used. The molecular weight of said polysaccharide is preferably in the range from $10^4$ to $5 \times 10^6$.

The process for the preparation of the butyric esters according to the present invention uses preferably natural polysaccharides as source polysaccharides, raw materials that can be easily isolated from sources of natural origin and found in large amounts. The compounds of the invention can be prepared by means of an esterification reaction both in homogeneous and heterogeneous conditions, possibly in the presence of a catalyst.

The esterification can be carried out by using butyric acid or one of its activated forms, such as for example a corresponding ester, anhydride, and acyl-halide.

Thanks to the esterification reaction described above, it is possible to obtain butyric esters with different degrees of substitution (DS) by operating with adequate temperature and reaction times and by using suitable molar ratios among the reagents.

The butyric esters of polysaccharides according to the present invention exert a high antiproliferative activity, which makes them useful in the treatment of diseases characterized by abnormal cell proliferation. An example of these diseases is represented by neoplasms: the present compounds are thus useful in the treatment and prevention of tumors. The preventive treatment of tumors is extended to the treatment of conditions susceptible of neoplastic degeneration, like inflammatory intestinal diseases, diverticulosis, Crohn's disease, inflammatory colitis, ulcerative colitis; the possibility of neoplastic degeneration of these diseases is known in the prior art (cf. J. Cell.Biochem.Suppl., 1992, 16G:47–50; Dis.Colon Rectum, 1991, 34(2), 174–180).

Another example of application is represented by the treatment of synovial cell proliferation. This condition is present in a number of articular diseases like rheumatoid arthritis, juvenile arthritis, psoriatic arthritis. The proliferation of synoviocytes results in the degeneration of articular cartilage, bones and tendons (J. Immunol.1993, 151(9), 4908–4917). The compounds of the present invention are able to effectively revert the synovial cell proliferation, thus countering the development of the above disorders.

Further conditions characterized by abnormal cell proliferation, like e.g. psoriasis, hyperkeratosis, prostatic hyperplasia can be treated and prevented by using the compounds of the present invention.

For the above butyric esters, the systemic administration either oral or parenteral, topical or transdermal is advisable. Said esters are preferably administered by the following routes of administration: oral, intravenous, intraperitoneal, intraarticular, intramuscular, rectal, intravaginal.

The therapeutically effective dose varies according to the administration route as well as to the seriousness of the pathology. Moreover, it varies also in relation to age, weight and general state of health of the patient.

The therapeutically effective dose varies preferably from 0.2 to 500 mg/kg/day for 1–15 days.

In case of intravenous injections, said butyric ester is preferably administered in doses of 0.2–50 mg/kg/day for 8–12 days. If injected intraperitoneally, said butyric ester is preferably administered in the form of a solution or aqueous suspension, and even more preferably in a physiological buffer, in the amount of 1–100 mg/kg/day and even more preferably 10–50 mg/kg/day for 8–12 days. Finally, for oral administration, said butyric ester is preferably administered in the amount of 300–500 mg/kg/day for 8–12 days.

The new butyric esters of the invention, obtained by means of partial or total esterification, with butyric acid, of the free hydroxyl groups of the saccharidic residue of the polysaccharides, evidence a surprising increase of the antiproliferative activity of the source polysaccharides and of the butyric acid, known in the state of the art for their antineoplastic activity. The antiproliferative activity exerted by the new butyric esters of the invention is surprisingly higher than the theoretical sum of the effects of both components, thus evidencing an unexpected synergy of action of the butyric acid and of the polysaccharide, which are bound to one another by means of ester bond. Therefore, the new derivatives are different from the simple esters of the butyric acid known in the state of the art, merely used as pro-drugs broadening the half-life of the butyric acid.

In the examples shown below, the biological activity of the new butyric esters of the invention and their antiproliferative activity were tested on several tumor lines.

Finally, the present invention comprises new pharmaceutical compositions containing a therapeutically effective amount of at least one of the butyric esters of the invention. These pharmaceutical compositions are preferably in the form of injectable solutions or suspensions for the systemic, intravenous, intraperitoneal, intraarticular, hypodermic or intramuscular administration. In this case, the formulations can be prepared just before use, by solubilization or suspension of the esters of the invention in the form of lyophiles in suitable diluents.

For the oral administration, the solid preparations such as granules, tablets, pills and capsules are preferred as well as the semisolid form such as gels. Besides, the above formulations can include said butyric esters in combination with other antitumour drugs of common clinical use, such as for example 5-fluoruoracyl, cisplatin and cyclophosphamide which can be used in polychemotherapeutical protocols.

Some illustrative but not limitative examples of the preparation and activity of said butyric esters, according to the present invention, are hereunder reported.

EXAMPLE 1

Isolation of sulfated polysaccharide from *Grateloupia doryphora*.

5 g of *Grateloupia doryphora* collected in the Northern Adriatic Sea, in dry and milled form were suspended in 500 ml Milli-Q® water under stirring for 16 hours at 25° C. The extraction mixture underwent filtration under vacuum, through a 1,2 μm fiberglass membrane. The solution obtained was freezed in liquid nitrogen and then dried and 2 g of final product were obtained. The physico-chemical characteristics of the sulfated polysaccharide obtained from *Grateloupia doryphora* as described are as follows:

Molecular weight determination: the molecular weight of the polysaccharide obtained was determined according to the method described hereunder.

20 mg of the polysaccharide were weighed in a 10 ml flask; this flask was filled up to ⅔ of the total volume with 0.15M NaCl, the solution underwent magnetic stirring, at room temperature, up to its complete solubilization and then 0.15M NaCl was added up to the final total volume of 10 ml. The solution obtained was then filtered on 0.45 μm filters (MILLEXD filtering units, Millipore, cod. SLHA 025 NB, 1996), it was injected directly into a set of size-exclusion chromatographic columns (TSK-G600 $PW_{x1}$, TSK-G500 $PW_{x1}$ and TSK-G3000 $Pw_{x1}$, Tosohaas, respectively cod. 08024, 08023 and 08021, 1995) The molecular weights of the fractions eluted from the columns set were then acquired by the RI410 (Waters) refraction index.

For the determination of the molecular weight and of the molecular weight distribution, a "broad standard" calibration (based on a standard polysaccharide) was used. The acquisition and computing system (Chromstar, Rev. 3.13, Bruker Spectro) was implemented on a PC 486 IBM compatible. The average molecular weight of the polysaccharide was 251.000, while the refraction and polydispersity indexes were 4.2.

$^1$H-NMR: the structure of the polysaccharide obtained as described above was determined by NMR. The following repeating dimeric structures were identified:

3→[O-β-D-galactopyranosyl-4-sulfate-(1→4)-O-α-D-galactopyranosyl-3,6-anhydro] →1;

3→[O-β-D-galactopyranosyl-4-sulfate- (1→4)-O-α-D-galactopyranosyl-3,6-anhydro-2-sulfate] →1;

3→[O-β-D-galactopyranosyl-4- -(1→4)-O-α-D-galactopyranosyl-3,6-anhydro-] →1;

3→[O-β-D-galactopyranosyl-4- -(1→4)-O-α-L-galactopyranosyl-3,6-anhydro-] →1.

Sulfation degree determination:: the degree of sulfation of the polysaccharide obtained as described above was determined according to the following colorimetric method.

Milli-Q® water was used.

The A reagent (buffer solution of $BaCl_2$) was obtained by mixing 10 ml of acetic acid 2M in water, 2 ml of $BaCl_2$ $2H_2$ 0.01M in water and 8 ml of $NaHCO_3$ 0.02M in water and finally by adding absolute EtOH up to 100 ml The B reagent (solution of sodium rhodizonate) was prepared by dissolving 5 mg of sodium rhodizonate (Fluka, cod. 71940, 1995) in 20 ml of water, by adding 100 mg of ascorbic acid and by adding absolute EtOH up to the volume of 100 ml.

The A and B reagents solutions were kept in the dark for 30 minutes before use.

For the determination of the amount of sulfate present in the compound, suitable standard solutions of $SO_4^{2-}$, in $H_2SO_4$ to 96% and a blank solution prepared with water were used. A calibration curve was obtained by mixing 2 ml of absolute EtOH, 1 ml of A reagent and 1.5 ml of B reagent with the standard solution of $SO_4^{2-}$ and with the blank solution. After stirring, the solutions obtained were left in the dark, at room temperature for 10 minutes. The absorbance at 520 nm was then recorded, by regarding the blank as zero, by UV-VIS CARY 3E spectrophotometer (Varian).

Before carrying out the quantitative analysis of the sulfate group in the polysaccharide, the polysaccharide underwent hydrolysis.

A Pyrex-glass bakelite-sealed test-tube containing 3.00 mg of polysaccharide in 1 ml of HCl was kept in the oven for 4 hours at the temperature of 120° C., and the complete hydrolysis of the sulfate groups was obtained. Several measurements carried out at different times of hydrolysis have evidenced that prolonged heating for 3–4 hours is sufficient to obtain the complete hydrolysis of the sulfate groups.

After such time, the sample was transferred into a rotary evaporator. The bath temperature was kept at about 50° C. so as to eliminate HCl. The solution obtained was then added with water so as to obtain a final concentration of hydrolyzed sample of 2 mg/ml. After treating the hydrolyzed sample with reagents A and B, as described for the sulfate samples used for the calibration curve, the absorbance at 520 nm was read and the amount of sulfate was determined by using the angular coefficient of the calibration curve. The above analysis revealed that the content of sulfate groups was 31% w/w.

EXAMPLE 2

Preparation of the butyric ester of hyaluronic acid having a degree of substitution, DS :0.08.

0.2 g of hyaluronic acid (($4\times10^4$MW) were weighed in a 250 ml round-bottom flask provided with a stirring apparatus and dissolved in 25 ml de-ionized water. The solution was acidified with 0.23 ml of HCl and, after five minutes, 0.132 ml of collidine was added. After 5 minutes, the solution was concentrated down to a volume of about 15 ml under vacuum. 60 ml of anhydrous DMF was then added and the system was concentrated down to about 40% of its initial volume. The last two steps were repeated once more. The mixture were diluted with 40 ml of DMF followed by addition of 0.2 ml of pyridine and 0.163 ml of butyric anhydride. The reaction was carried out at room temperature and stopped for 18 hours. The solution underwent concentration under vacuum and then 50 ml of de-ionized water was added. The pH of the solution was then adjusted to about 6.5–7 with aqueous $NaHCO_3$ followed by dialysis against de-ionized water (4×2 l). The product was recovered by freeze-drying and 0.135 g of butyrate derivative were obtained.

The physico-chemical features of the butyrated hyaluronic acid, obtained as described above, are as follows:

$^1$H-NMR: in addition to the typical signals of hyaluronic acid, some 0.90 ppm, 1.62 ppm and 2.39 ppm signals can be detected, which can be assigned respectively to the protons of the methyl and methylenic groups of butyrate.

The degree of esterification was estimated on the basis of the NMR spectrum; the percentage of the butyric esters was then determined by integration of the signal related to the methyl group with respect to the signal of the N-acetyl group of hyaluronic acid. Following this procedure 16% of the disaccharidic repeating unit of hyaluronic acid was substituted with butyric residues, with a corresponding DS of 0.08.

EXAMPLE 3

Preparation of the butyric ester of hyaluronic acid having a degree of substitution, DS : 0.2 1.5 g of hyaluronic acid ($4\times10^4$MW), were weighed in a 1 l round-bottom flask provided with a stirring apparatus and dissolved in 50 ml de-ionized water. The solution was acidified with 1.71 ml of 2N HCl and after five minutes 0.993 ml of collidine was added. After 5 minutes, the solution was concentrated down to about half the volume under vacuum. 190 ml of anhydrous DMF was then added and the system was concentrated down to about 50–60 ml. Another 100 ml of anhydrous DMF was added. The solution was concentrated again. The mixture was then diluted with another 100 ml of DMF followed by addition of 2.85 ml of pyridine and 1.76 ml of butyric anhydride. The reaction was carried out at room temperature and stopped after 20 hours. The solution underwent concentration under vacuum and then the residue was suspended in 150 ml of de-ionized water. The pH of the solution was then adjusted to about 6.5 with aqueous $NaHCO_3$ and the solution was dialysed against de-ionized water (5×2 l). The product was recovered by freeze-drying and 1.04 of derivative was obtained.

The physico-chemical features of the butyrated hyaluronic acid, obtained as described above, are as follows:

$^1$H-NMR: in addition to the typical signals of hyaluronic acid, 0.90 ppm, 1.62 ppm and 2.39 ppm signals can be detected, which can be assigned respectively to the protons of the methyl and methylenic groups of butyrate.

By applying the method described in example 2, 40% of the disaccharidic repeating unit of hyaluronic acid was substituted with butyric residues, with a corresponding DS of 0.2.

EXAMPLE 4

Preparation of the butyric ester of hyaluronic acid having DS: 0.075.

were added to a solution 2.0 g of hyaluronic acid ($4\times10^4$ MW) were weighed in a 1 l round-bottom flask in 60 ml deionized water. The solution was acidified with 2.30 ml of 2N HCl and after five minutes 1.32 ml of collidine was added. The solution was concentrated down to about half the volume and then another 300 ml of anhydrous DMF was added so as to obtain the full solubilization of the polysaccharide. The solution was concentrated down to about 80 ml; another 200 ml of DMF was added and the solution was then newly concentrated.

The procedure described above was then repeated once more. After further addition of DMF (60 ml) to the mixture obtained in this way, 3.8 ml of pyridine and 1.634 of butyric anhydride was added, and the reaction was carried out at room temperature, for 16 hours. The solution was then dried under vacuum and the residue obtained was recovered with 120 ml of de-ionized water to obtain a dense syrup which was then suspended in 50 ml of de-ionized water. The pH of the solution was then adjusted to about 6.5–7 with aqueous $NaHCO_3$ and the solution was dialysed against de-ionized water (5×1 l). The product was recovered after freeze-drying and 1 g of product was obtained.

The physico-chemical features of the butyrated hyaluronic acid, obtained as described above, are as follows:

$^1$H-NMR spectrum: in addition to the typical signals of hyaluronic acid, 0.90, 1.62 and 2.39 ppm signals can be detected, which can be assigned respectively to the protons of the methyl and methylenic groups of butyrate.

According to the procedure described in Example 2, 15% of the disaccharidic repeating unit of hyaluronic acid was substituted with butyric residues with a corresponding DS: 0.075.

EXAMPLE 5

Preparation of the butyric ester of hyaluronic acid with DS: 0.06

A solution containing 1.5 g of hyaluronic acid ( MW $4\times10^4$), in 60 ml of de-ionized water was stirred for 5 minutes in a round bottom flask equipped with stirring apparatus and 1.71 ml of 2N HCl was then added. After further 5 minutes 0.99 ml of collidine was added and the resulting mixture was concentrated down to about half the volume. After addition of 250 ml of anhydrous DMF, the solution was concentrated down to about 80 ml and another 200 ml of DMF was added; the solution was then newly concentrated by repeating the procedure and a final addition of 150 ml was made. 2.85 ml of pyridine and 1.22 ml of butyric anhydride was added to the solution. The reaction was carried out t room temperature for 18 hours. The mixture underwent concentration under vacuum and then 150 ml of de-ionized water was added. The pH was adjusted to about 6.5 with $NaHCO_3$. The solution was dialysed against de-ionized water (5×1 l) and freeze-dried.; 1.32 g. of product was recovered.

The physico-chemical features of the butyrate of hyaluronic acid as described above are as follows:

$^1$H-NMR spectrum: in addition to the typical signals of hyaluronic acid, 0.90, 1.62 and 2.39 ppm signals can be detected, which can be assigned respectively to the protons of the methyl and methylenic groups of butyrate.

By using the method described in Example 2, 12% of the disaccharidic repeating unit of hyaluronic acid was substituted with butyric residues (DS:0.06).

EXAMPLE 6

Preparation of the butyric ester of hyaluronic acid with DS: 0.25

0.75 g of hyaluronic acid (MW $4\times10^4$) were weighed in a round bottom flask equipped with stirring apparatus and dissolved in 40 ml of de-ionized water. The solution was acidified with 0.465 ml of 4N HCl and after 10 minutes 0.31 ml of collidine and 70 ml of DMF were added. The resulting mixture was concentrated to 90% of the volume. After addition of another 70 ml anhydrous DMF, the solution was concentrated down to 50% of the volume. The procedure was repeated twice. 70 ml of reagent was added each time. 40 ml of DMF, 3 ml of pyridine and finally 1.22 ml of butyric anhydride was then added in sequence to the mixture. The reaction was carried out at room temperature and stopped after 17 hours. After addition of 3 ml of pyridine and 0.56 of succinic anhydride, the mixture was kept at room temperature for 6 hours, and was heated at 70° C. for a period of 16 hours. The solution was then concentrated under vacuum and the residue was then dissolved in water. The pH of the solution was adjust to 6–6.5 with aqueous $NaHCO_3$, and the solution was dialysed against de-ionized water (5×2 l). The product was recovered after freeze drying and 0.8 g of derivative was obtained.

The physico-chemical features of the hyaluronic acid derivative esterified with butyric acid and succinic anhydride obtained as described above, are as follows:

$^1$H-NMR spectrum: in addition to the typical signals of hyaluronic acid, 0.90, 1.62 and 2.39 ppm signals can be detected, which can be assigned respectively to the protons of the butyric groups.

By using the method described in Example 2, 50% of the disaccharidic repeating unit of hyaluronic acid was substituted with butyric residues (DS: 0.25) while 70% of the disaccharidic repeating unit was succinylated (DS: 0.35).

EXAMPLE 7

Preparation of the butyric ester of hyaluronic acid having a DS: 0.3, by homogeneous-phase process.

Hyaluronic acid (0.10 g) having a $4\times10^4$ MW, was suspended in 10 ml DMSO, and few drops of HCl (37%) were added to adjust the pH to 4–5 value. The mixture was then kept under magnetic stirring at room temperature until complete dissolution. Then 0.40 g of dimethylaminopyridine and 1.14 ml of butyric anhydride were added to the solution, and the mixture was kept under constant stirring for 18 hours at room temperature. The pH of the solution was then raised to about 5–6 with aqueous $NaHCO_3$ and the solution was dialysed against de-ionized water (5×l). The solution was then finally freeze-dried and 0.04 g of butyrate derivative were obtained in the form of a lyophile.

The physico-chemical features of the butyrated hyaluronic acid, obtained as described above, are as follows:

$^1$H-NMR: in addition to the typical signals of hyaluronic acid, 0.90 ppm, 1.62 ppm and 2.39 ppm signals can be detected, which can be assigned respectively to the protons of the methyl and methylenic groups of butyrate.

The degree of esterification was determined on the basis of the NMR spectrum; the percentage of the butyric esters was then determined by integration of the signal related to the methyl group with respect to the signal of the N-acetyl group of hyaluronic acid. On the basis of this spectrum the DS is 0.3.

EXAMPLE 8

Preparation of the butyric ester of polysaccharide isolated from *Grateloupia doryphora* with DS: 0.1.

0.2 g of the sulfated polysaccharide, isolated from *Grateloupia doryphora* as described in Example 1, were dissolved in de-ionized water (10 ml) in a round bottom flask equipped with stirring apparatus and 0.117 ml of 4N HCl was added to the solution cooled at 5° C. The solution was kept under stirring for five minutes and another 0.99 ml of collidine was added. After 15 minutes, another 30 ml of anhydrous DMF was added and the solution obtained in was concentrated down to about 30% of the initial volume. After addition of another 30 ml of DMF, the solution was kept under stirring at the temperature of 5° C., for one hour and 2 ml of pyridine and 0.175 ml of butyric anhydride were added. The reaction was carried out at room temperature and stopped after 42 hours. It was then concentrated so as to obtain a dense mixture. This syrup was then dissolved in 75 ml of de-ionized water for 45 minutes. After adjusting the pH to 6 with $NaHCO_3$, the solution was dialysed against de-ionized water (2×2 l, 1×1 l) and finally freeze-dried. 0.19 g of product were recovered.

The physico-chemical features of the butyrate of sulfated polysaccharide obtained from *Grateloupia doryphora*, obtained as described above are as follows:

$^1$H-NMR spectrum: the degree of substitution was carried out by integrating the signals in the region from 5.5 and 5.0 ppm, assigned to the anomeric protons of saccharidic residues in α configuration, and the signal to about 1.0 ppm, assigned to the methylic protons of butyrate. From the ratio between the integrals, it is possible to maintain that the residues of butyric acid are 20% with respect to the saccharidic repeating unit in α configuration (DS: 0.1).

Colorimetric analysis: this analysis revealed an amount of sulfated groups of 31% w/w, like in the source polysaccharide as prepared in Example 1.

EXAMPLE 9

Preparation of the butyric ester of scleroglucan 0.5 g of scleroglucan (MW $7\times10^5$) were dissolved in 75 ml anhydrous DMF in a round bottom flask equipped with stirring apparatus. The mixture obtained was heated for one hour at the temperature of 50° C., and then was kept under stirring at the temperature of 70° C. for three hours. The solution was cooled down to 55° C. and then 0.25 ml of pyridine and 0.15 g of succinic anhydride were added. The mixture obtained was kept under stirring at the temperature of 55° C. for 64 hours. The mixture was then concentrated to obtain a dense syrup, which was then re-suspended in 75 ml of de-ionized water. After adjusting the pH to 6 with $NaHCO_3$, the mixture was dialysed against de-ionized water (4×2 l).

The solution obtained in this way was then filtrated and freeze-dried. The lyophile was dissolved in 20 ml of water in 60 minutes in a round bottom flask equipped with stirring apparatus. After addition of 0.65 ml of 2N HCl, the solution became white and opaque and was kept under stirring for five minutes. 1 ml of pyridine was then added and the solution was left under stirring for 10 minutes at a pH of 4–5. 75 ml of anhydrous DMF was added and the mixture was concentrated to a volume of 72 ml. The procedure was repeated once more, and 70 ml of solution were removed. After addition of 30 ml of DMF and 2 ml of pyridine, the mixture was kept at room temperature, for 15 minutes. 0.38 ml of butyric anhydride was added and the reaction was carried out at room temperature for 18 hours. After concentration, the residue was re-suspended in water and its pH was adjusted to 6.9 with aqueous $NaHCO_3$. The mixture obtained in this way was freeze-dried and then frozen. 0.196 g of were obtained.

EXAMPLE 10

Preparation of the butyric ester of pectin having DS: 1.7 0.93 g of pectin having a degree of esterification: 65%, were suspended in 50 ml DMSO under magnetic stirring at room temperature. After two hours, 0.85 g of dimethylaminopyridine was added. The mixture was kept under constant stirring at room temperature overnight. Then 3.26 ml of butyric anhydride was added, and the mixture was kept under constant stirring for 30 minutes at room temperature. Then suspension was heated at 80–100° C. for 20 hours. Finally, the pH of the solution was then raised to about 6.7 with aqueous $NaHCO_3$ and the solution was dialysed against de-ionized water (6×2 l). The suspension was centrifuged at 10000 rpm for 1 hour. The pellet was then collected was then finally freeze-dried and 0.9 g of butyrate derivative were obtained in the form of a lyophile. The physico-chemical features of the butyrated pectin, obtained as described above, are as follows:

$^1$H-NMR: in addition to the signals of pectin, some 0.90 ppm, 1.62 ppm and 2.39 ppm signals can be detected, which can be assigned respectively to the protons of the methyl and methylenic groups of butyrate.

The degree of esterification was determined on the basis of the NMR spectrum; the percentage of the butyric esters was then determined by integration of the signal related to the methyl group with respect to the signal of the methyl ester group of pectin (3.63 ppm). On the basis of this spectrum, DS is 1.7.

BIOLOGICAL ACTIVITY TESTS

EXAMPLE 11

Test of in vitro antiproliferative activity

Materials and Methods

The antiproliferative activity of the butyric esters of the invention was tested on several tumor cell lines and in particular:

MCF7: cells of hormone-dependent mammary carcinoma;
MDA-MB231: cells of hormone-dependent mammary carcinoma;
IGROV1: cells of ovary carcinoma;
HeLa: cells of the cervix carcinoma;
CaLu: cells of lung carcinoma;
HT29: cells of colon carcinoma.

The above cell lines were grown as monolayer on DMEM/F12 Dulbecco-modified Eagle's medium (Sigma Chemical Co., St. Louis) supplemented with 2% v/v FCS (fetal calf serum), in a T-75 $cm^2$ plastic bottle (Corning Industries, Corning, N.Y.) kept at the temperature of 37° C., under damp atmosphere containing 5% of $CO_2$. They are transferred weekly into a fresh medium. Before the beginning of the experimental tests, the cells in the exponential growth phase were removed from the flasks with a solution of 0.05% trypsin and 0.02% EDTA. The cells were then seeded in 12-welled dishes (50.000 cells/well) on DMEM/F12 medium supplemented with 2% FCS. The cells were then grown for 24 hours, in order to promote the adhesion, and the medium was then removed and replaced with the experimental medium. The cells were then kept for 6 or 9 days on a DMEM/F12 medium supplemented with 2% FCS and several concentrations of the compounds in the Examples 2 and 4, according to the present invention, were added. A comparative test was carried out with hyaluronic acid with a MW of 4 $10^4$ added at the same concentrations.

The HeLa and CaLu cells were treated as described above for the other cell lines by using, instead of the DMEM/F12 medium supplemented with 2% FCS, respectively the DMEM/F12 medium supplemented with 10% FCS and 1% glutammine, in the HeLa case, and the RPMI 1640 medium supplemented with 10% FCS and 1% glutamine, in the case of CaLu.

The antiproliferative activity was determined by means of calorimetric determination of the DNA content variation (Burton method), which is proportional to the number of cells and is based on the calorimetric reaction between diphenylamine and the indolic groups of temperature-denatured DNA.

Results

Table 1 shows the growth percentage of the cell line of MCF7 mammary carcinoma, in the presence of butyric esters of polysaccharides, according to the present invention, with respect to the untreated cells (control), after 6 days of treatment. Each value results from the mean of 4 tests (was averaged after four tests), according to the factorial drawing 4×4.

The molarity of the butyric esters of the invention are referred to the molarity of butyrate which are present in the ester itself. As far as hyaluronic acid is concerned, the molarity is the same as the molarity of the compound in Example 2, where the same amount of hyaluronic acid is present.

|  | Concentration (mM) | | | | | | | |
|---|---|---|---|---|---|---|---|---|
| Compound | 0.016 | 0.032 | 0.064 | 0.125 | 0.25 | 0.5 | 1 | 2 |
| Hyaluronic acid | — | 86 | 81 | 80 | 78 | 78 | 60 | 30 |
| Example 3 | 90 | 78 | 76 | 76 | 74 | 74 | 48 | 13 |
| Example 4 | 101 | — | 76 | 75 | 74 | 51 | 25 | 8 |
| Example 6 | 78 | 68 | 61 | 58 | 57 | 39 | 18 | 5 |

*These experiments were carried out with a cell density equal to 25.000 cells/well.

From the figures reported above, it is evident that the butyric esters according to the present invention can exert an high antiproliferative activity with respect to the control and with respect to the non-esterified hyaluronic acid.

Table 2 shows the growth percentages of the cell lines of MCF7 mammary carcinoma, in the presence of butyric esters according to the present invention, after 6 days of treatment, with respect to the untreated cells (control), with respect to the non-butyrated natural polysaccharide extracted from *Grateloupia doryohora,* as described in Example 1, and with respect to the non-esterified scleroglucan, used as a source product in the synthesis described in Example 9.

Even in this case, each value was averaged after 4 tests, placed on the dish according to the factorial drawing 4×4. The concentrations of the compounds tested are expressed as mg of compound/ml of total solution.

|  | Concentration (mM) | | | | |
|---|---|---|---|---|---|
| Compound | 0.001 | 0.01 | 0.1 | 1 | 2 |
| Example 1 | 87 | 85 | 62 | 41 | 34 |
| Example 7 | 72 | 71 | — | 36 | 5 |
| Scleroglucan | 86 | 79 | 75 | 54 | 32 |
| Example 9 | — | — | 57 | 32 | 5 |

The figures show that the butyric esters reported above can exert an high antiproliferative activity with respect to the blank, to the polysaccharide in Example 1 and to the scleroglucan.

Figure 1:
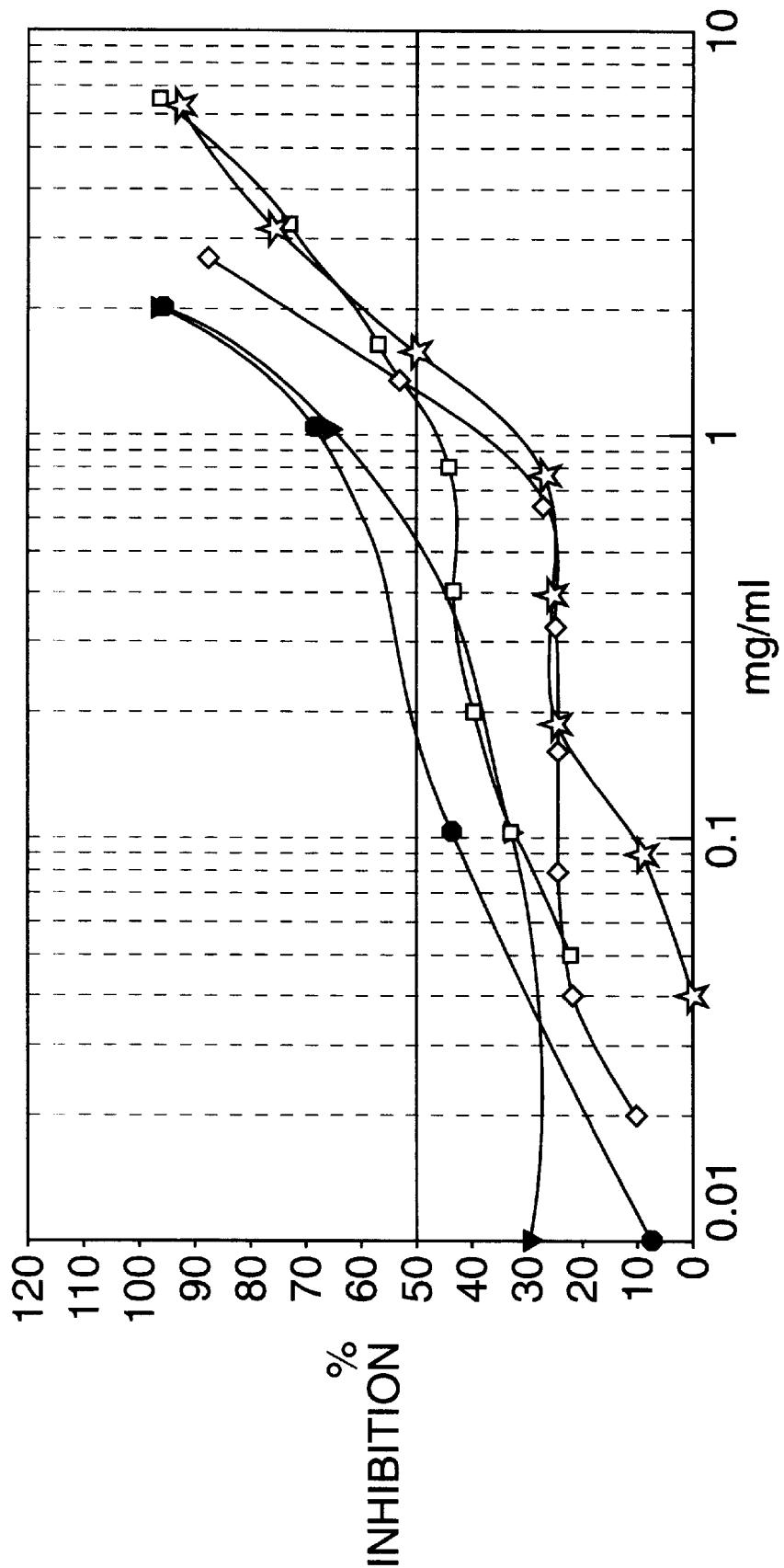
FIG. 1 shows the figures reported above as related to the antiproliferative activity of the compounds in Example 3, 4 and 7–9 according to the present invention, in a graphic form, by evidencing the inhibition percentage of the tumor cells proliferation as a function of the concentration of the tested compounds (expressed as mg of compound/ml of total solution).

FIG. 1 shows the figures reported above as related to the antiproliferative activity of the compounds in Example 3, 4 and 7–9 according to the present invention, in a graphic form, by evidencing the inhibition percentage of the tumor cells proliferation as a function of the concentration of the tested compounds (expressed as mg of compound/ml of total solution).

Moreover, Table 3 shows the values of IC50 (necessary concentration to inhibit the cell growth by 50%) of the butyric esters according to the present invention, after 6 days of treatment of the different tumor cell lines. The concentrations of the esters of the invention are expressed both as molarity of the butyrate present in the ester itself (mM) and as mg of the compound/ml of total solution (mg/ml).

|  | Example 3 | | Example 4 | |
|---|---|---|---|---|
| Cell Line | (mM) | (mg/ml) | (mM) | (mg/ml) |
| MFC7 | 1 | 1.3 | 0.5 | 1.6 |
| MDA-MB231 | 0.55 | 0.7 | 0.7 | 1.2 |
| IGROV1 | 0.46 | 0.6 | 0.41 | 1.3 |
| HeLa | 0.45 | 0.6 | 0.56 | 1.9 |
| CaLu | — | — | 0.9 | 2.9 |
| HT29 | 1.8 | 2.3 | 0.7 | 2.1 |

EXAMPLE 12

In vitro antiproliferative activity of the butyrate of hyaluronic acid as described in Example 2 with respect to the single components (hyaluronic acid and butyric acid) and their physical mixture.

Materials and Methods

Cells of the MCF7 lines of hormone-dependent mammary carcinoma, treated and cultured as described in Example 11, were kept for 6 days on a DMEM/F12 medium supplemented with 2% FCS, in the presence of different concentrations of the butyric ester of Example 2, according to the present invention, of its components, that is hyaluronic acid (MW: $4 \cdot 10^4$), with butyric acid and of the physical mixture of hyaluronic acid and butyric acid.

The anti-proliferative activity was determined according to the Burton method, as described in Example 11.

Results

Table 4 shows the antiproliferative activity of the butyrate of hyaluronic acid as described in Example 2 on the growth of the MCF7 cell lines, after 6 days of treatment, as a comparison to the effect of hyaluronic acid, of sodium butyrate and of the physical mixture of both components, used at the same concentrations and experimental conditions.

The figures reported above give the inhibition percentage of the cell growth, with respect to the untreated cell (control). The molarities (mM) are referred to the molarities of the examined compounds; as for hyaluronic acid, the molarity indicates the same quantity of hyaluronic acid in the butyric ester as described in Example 2 where the molarity value is referred to the butyrate concentration.

|  | Concentration (mM) | | | | | | |
|---|---|---|---|---|---|---|---|
| Compound | 0.032 | 0.064 | 0.125 | 0.25 | 0.5 | 1 | 2 |
| Example 2 | 20 | 33 | 42 | 53 | 83 | 92 | 96 |
| sodium butyrate | 11 | 15 | 20 | 28 | 39 | 55 | 78 |
| Hyaluronic acid | 14 | 19 | 23 | 31 | 41 | 59 | 60 |

-continued

| Compound | Concentration (mM) | | | | | | |
|---|---|---|---|---|---|---|---|
| | 0.032 | 0.064 | 0.125 | 0.25 | 0.5 | 1 | 2 |
| sodium butyrate and hyaluronic acid | 5 | 20 | 27 | 35 | 47 | 52 | 51 |

FIG. 2 illustrates the figures reported above in a representation which shows the inhibition percentage of the cell growth vs the concentration of the compounds tested.

These figures show that the butyric esters of polysaccharides can exert an antiproliferative activity which is unexpectedly higher than the activity exerted by the mixture of the components.

EXAMPLE 13

In vitro antiproliferative activity of the butyric esters of Example 3 and 4 with respect to the sodium butyrate.

Materials and Methods

Cells of mammary carcinoma of the hormone-dependent MDA-MB231 line, treated and cultivated as described in Example 11, were kept for 6 days on DMEM/F12 medium supplemented with 2% FCS in the presence of different concentrations of butyric esters as in Example 3 and 4, according to the present invention and of sodium butyrate.

The antiproliferative activity was determined according to the Burton method, as described in Example 11.

Results

FIG. 3 shows the antiproliferative effect of the butyric ester of Examples 3 and 4 on the growth of the MDA-MB231 cell line, after 6 days of treatment, as a comparison of the effect of sodium butyrate used at the same concentrations and experimental conditions. The diagram shows the inhibition percentage of the cell growth vs the concentration of the compounds tested the (mM) molarity is referred to the concentration of (the butyrate in the compounds examined).

What is claimed is:

1. The butyric ester of a polysaccharide, where the hydroxyl groups of said polysaccharide are partially or totally esterified with butyric residues, said polysaccharide being selected from the group consisting of hyaluronic acid, $\beta(1\rightarrow3)$-D-glucan and sulfated polysaccharide extracted from Grateloupia doryphora.

2. The butyric ester according to claim 1, characterized by the fact that the free hydroxyl groups of the glycosidic residue of said polysaccharide are esterified with one or more dicarboxylic residues.

3. The butyric ester according to claim 2, characterized in that said dicarboxylic acid residues are $C_2$-$C_9$.

4. The butyric ester according to claim 3, characterized by the fact that said dicarboxylic acids are selected from the group consisting of succinic, tartaric, malic and azelaic acids.

5. The butyric ester according to claim 1, characterized by the fact that the number of hydroxyl groups esterified with butyric residues, for each glycosidic monomer is higher than 0.001.

6. The butyric ester according to claim 5, characterized by the fact that the number of hydroxyl groups esterified with butyric residues ranges from 0.001 to 3.

7. The butyric ester according to claim 6, characterized by the fact that the number of hydroxyl groups esterified with butyric residues ranges from 0.01 to 1.

8. The butyric ester according to claim 7, characterized by the fact that the molecular weight of said $\beta(1\rightarrow3)$-D-glucan ranges from $1\times10^4$ to $1\times10^6$.

9. The butyric ester according to claim 7, characterized by the fact that the molecular weight of said hyaluronic acid ranges from $1\times10^4$ to $2\times10^6$.

10. The butyric ester, according to claim 1, characterized by the fact that the molecular weight of said butyric ester is higher than $2\times10^3$.

11. The butyric ester, according to claim 10, characterized by the fact that the molecular weight of said polysaccharide extracted from Grateloupia doryphora ranges from $1\times10^4$ to $5\times10^6$.

12. The butyric ester according to claim 1, characterized by the fact that said $\beta$-$(1\rightarrow3)$-D glucan further contains $\beta$-$(1\rightarrow6)$-glucosidic residues.

13. The butyric ester according to claim 12, characterized by the fact that said glucan is scleroglucan.

14. A pharmaceutical composition for the treatment of diseases characterized by abnormal cell proliferation containing as an active compound a therapeutically effective quantity of at least one butyric ester of a polysaccharide as described in claim 1 in combination with pharmaceutically acceptable excipients and/or diluents.

15. The pharmaceutical composition according to claim 14, characterized by the fact that it can be administered orally in the form of granules, tablets, pills or gel.

16. The pharmaceutical composition according to claim 14, characterized by the fact that it can be administered via the following administration routes: systemic, intravenous, intraperitoneal, intraarticular, subcutaneous or intramuscular, in the form of an aqueous solution or suspension.

17. The pharmaceutical composition according to claim 14, characterized by the fact that it includes also one or more antitumor drugs.

18. The pharmaceutical composition according to claim 17, where the antitumour drug is selected from the group consisting of 5-fluoruoracyl, cisplatin and cyclophosphamide.

19. A method for treating diseases characterized by abnormal cell proliferation, characterized by administering to a patient in need thereof a therapeutically effective amount of a butyric ester of a polysaccharide, whose hydroxyl groups are partially or totally esterified with butyric residues.

20. The method according to claim 19, where the proliferation involves neoplastic cells or synovial cells or cells of the gastrointestinal tract.

21. The method according to claim 19, characterized by the fact that said butyric ester is administered via the following administration routes: oral, intravenous, intraperitoneal, intramuscular, interarticular, rectal, intravaginal, subcutaneous or topical.

22. The method according to claim 19, characterized by the fact that said butyric ester is administered in doses ranging from 0.2 and 500 mg/kg/day for a period from 1 to 15 days.

* * * * *